(12) United States Patent
Hirata

(10) Patent No.: US 11,398,061 B2
(45) Date of Patent: Jul. 26, 2022

(54) IMAGE INFORMATION PROCESSING APPARATUS, DISPLAY METHOD AND NON-TRANSITORY COMPUTER-READABLE MEDIUM

(71) Applicant: CANON KABUSHIKI KAISHA, Tokyo (JP)

(72) Inventor: Yoshihiro Hirata, Fuchu (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 11 days.

(21) Appl. No.: 16/885,840

(22) Filed: May 28, 2020

(65) Prior Publication Data

US 2020/0294276 A1 Sep. 17, 2020

Related U.S. Application Data

(63) Continuation of application No. PCT/JP2018/043721, filed on Nov. 28, 2018.

(30) Foreign Application Priority Data

Dec. 1, 2017 (JP) .............................. JP2017-231656

(51) Int. Cl.
  *G06T 11/00* (2006.01)
  *G06T 7/70* (2017.01)
  *G06T 5/50* (2006.01)
  *G06T 7/60* (2017.01)

(52) U.S. Cl.
  CPC ................ *G06T 11/00* (2013.01); *G06T 5/50* (2013.01); *G06T 7/60* (2013.01); *G06T 7/70* (2017.01); *G06T 2200/24* (2013.01); *G06T 2207/20221* (2013.01); *G06T 2207/30204* (2013.01)

(58) Field of Classification Search
  None
  See application file for complete search history.

(56) References Cited

U.S. PATENT DOCUMENTS

2015/0058368 A1* 2/2015 Hyde ..................... G16H 20/10
  707/756
2015/0119684 A1* 4/2015 Furukawa .............. A61B 5/004
  600/407

(Continued)

FOREIGN PATENT DOCUMENTS

| JP | 2012-135368 A | 7/2012 |
| JP | 2017-897 A | 1/2017 |
| WO | 2010/030817 A1 | 3/2010 |

*Primary Examiner* — Yanna Wu
(74) *Attorney, Agent, or Firm* — Venable LLP

(57) ABSTRACT

An image information processing apparatus includes a photoacoustic image acquisition unit configured to acquire an photoacoustic image generated based on a photoacoustic wave by irradiating a subject and a marker with light, an optical image acquisition unit configured to acquire an optical image generated by optically capturing an image of the subject and the marker; and an image processing unit configured to generate a superimposed image in which the photoacoustic image and the optical image are superimposed and display the superimposed image on a display unit. The image processing unit generates the superimposed image based on the marker in the photoacoustic image and the marker in the optical image.

23 Claims, 11 Drawing Sheets

(56) References Cited

U.S. PATENT DOCUMENTS

2016/0135688 A1* 5/2016 Ebisawa .............. A61B 5/708
            600/407
2016/0363593 A1* 12/2016 Sebastiao ............. G01N 33/574
2019/0183347 A1   6/2019 Hirata

* cited by examiner

IMAGE INFORMATION PROCESSING APPARATUS, DISPLAY METHOD AND NON-TRANSITORY COMPUTER-READABLE MEDIUM

CROSS-REFERENCE TO RELATED APPLICATIONS

This application is a Continuation of International Patent Application No. PCT/JP2018/043721, filed Nov. 28, 2018, which claims the benefit of Japanese Patent Applications No. 2017-231656, filed Dec. 1, 2017, which is hereby incorporated by reference herein in their entirety.

BACKGROUND OF THE INVENTION

Field of the Invention

The present invention relates to an image information processing apparatus, a display method and non-transitory computer-readable medium.

Description of the Related Art

A photoacoustic effect, where an acoustic wave (photoacoustic wave) is generated when a subject is irradiated with pulsed light which is generated from a light source, is known. Photoacoustic imaging is a technique to image the inside of a subject using a photoacoustic wave, and acquire a photoacoustic image (e.g. vascular image) which reflects the optical characteristics of the subject.

A subject inspection apparatus according to PTL 1 includes a hemispherical support body where a plurality of conversion elements, which receive an acoustic wave generated inside the subject and convert the acoustic wave into an electric signal, are disposed. The subject is held by a thin cup-shaped holding member, and an acoustic matching medium, such as water, is disposed between the holding member and the conversion elements. When light is emitted from the bottom of the support member, the light reaches the subject via the acoustic matching medium and the holding member, whereby a photoacoustic wave is generated. The conversion elements disposed in the support body receive the photoacoustic wave via the holding member and the acoustic matching medium.

When a user compares a photoacoustic image and a subject, the positional relationship between the photoacoustic image and the actual subject may be difficult to recognize in some cases. For example, compared with a palm, a femoral region is wide and has less characteristics on the surface. Therefore it is relatively difficult to recognize which part of the femoral region that corresponds to the photoacoustic image.

With the foregoing in view, it is an object of the present invention to provide a technique to easily recognize the correspondence between a photoacoustic image and a subject.

CITATION LIST

Patent Literature

[PTL 1] WO 2010/030817

SUMMARY OF THE INVENTION

The present invention employs the following configuration. Namely, it is provided an image information processing apparatus, including:

a photoacoustic image acquisition unit configured to acquire a photoacoustic image generated based on a photoacoustic wave by irradiating a subject and a marker with light;

an optical image acquisition unit configured to acquire an optical image generated by optically capturing an image of the subject and the marker; and an image processing unit configured to generate a superimposed image in which the photoacoustic image and the optical image are superimposed and display the superimposed image on a display unit, wherein the image processing unit generates the superimposed image based on the marker in the photoacoustic image and the marker in the optical image.

Additionally, the present invention employs the following configuration. Namely, it is provided a display method, including:

a photoacoustic image acquisition step of acquiring a photoacoustic image generated based on a photoacoustic wave by irradiating a subject and a marker with light;

an optical image acquisition step of acquiring an optical image generated by optically capturing an image of the subject and the marker; and an image processing step of generating a superimposed image in which the photoacoustic image and the optical image are superimposed and display the superimposed image on a display unit, wherein the image processing step generates the superimposed image based on the marker in the photoacoustic image and the marker in the optical image.

Further features of the present invention will become apparent from the following description of exemplary embodiments with reference to the attached drawings.

DESCRIPTION OF THE EMBODIMENTS

Figure 1:
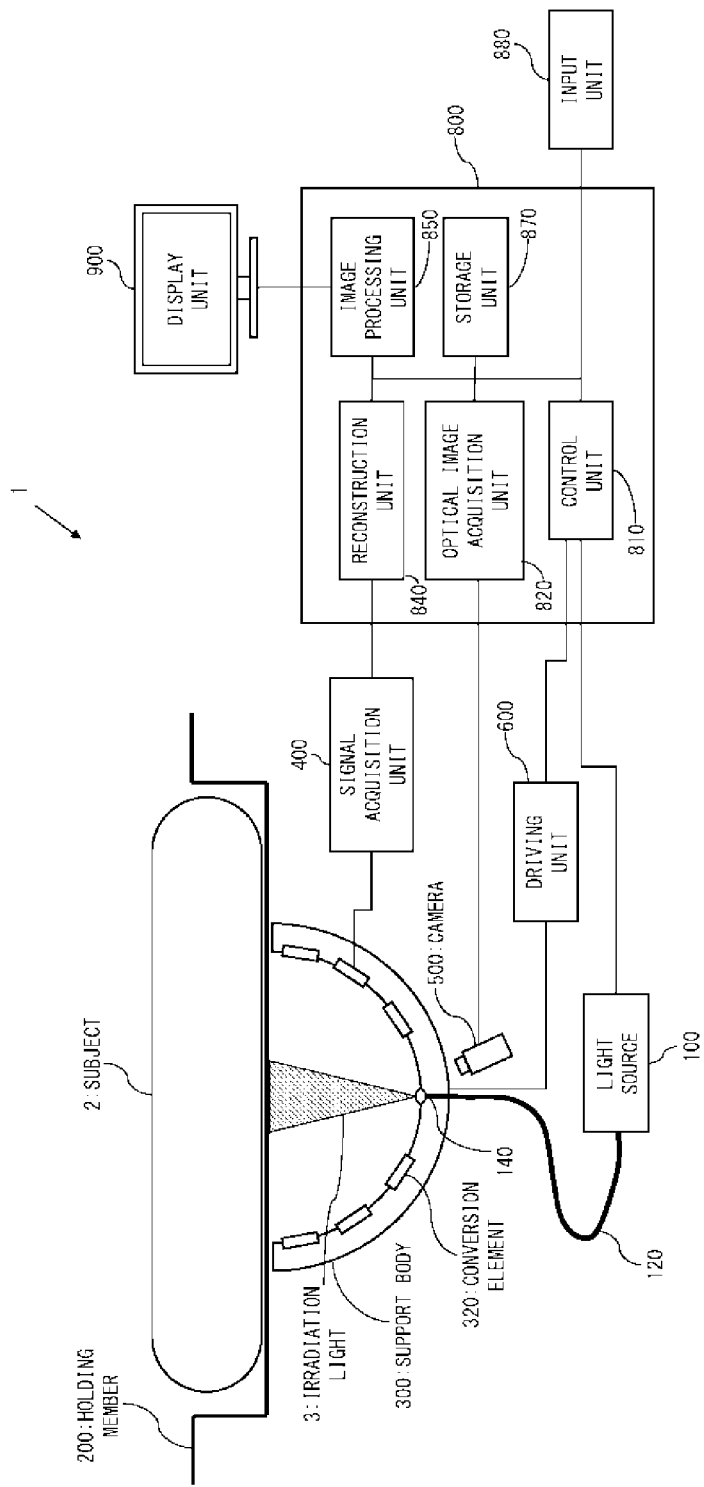
FIG. 1 is a conceptual diagram of a subject information acquisition apparatus according to Embodiment 1.

Preferred embodiments of the present invention will be described with reference to the drawings. Dimensions, materials, shapes, relative positions of the components, etc., described below should be appropriately changed depending on the configurations and various conditions of the apparatus to which the invention is applied. Therefore the following description is not intended to limit the scope of the invention.

The present invention relates to a technique to detect an acoustic wave propagating from an object, and generate and acquire the characteristic information inside the subject (subject information). This means that the present invention is regarded as a photoacoustic apparatus or a control method thereof, or as a subject information acquisition apparatus, or a control method thereof. The present invention is also regarded as an image information processing apparatus or a control method thereof, or as an image processing method. The present invention is also regarded as a subject information acquisition method or a signal processing method. Further, the present invention is regarded as a program that causes an information processing apparatus, equipped with such hardware resources as a CPU and memory, to execute these methods, or a computer readable non-transitory storage medium storing this program.

The subject information acquisition apparatus of the present invention includes a photoacoustic apparatus based on a photoacoustic effect that receives an acoustic wave generated inside the subject by irradiating the subject with light (electromagnetic wave), and acquires the characteristic information on the subject as image data. In this case, characteristic information refers to information on the characteristic values corresponding to each of a plurality of positions inside the subject, and this information is generated using the signals derived from the received photoacoustic wave. For example, the characteristic information is the generation source distribution of an acoustic wave generated by irradiation with light, the initial sound pressure distribution inside the subject, the optical energy absorption density distribution and absorption coefficient distribution derived from the initial sound pressure distribution, and the concentration distribution of a substance constituting a tissue. The concentration distribution of a substance refers to the oxygen saturation degree distribution, the total hemoglobin concentration distribution, the oxy/deoxy hemoglobin concentration distribution and the like.

The characteristic information, which is subject information at a plurality of positions, may be acquired as a two-dimensional or three-dimensional characteristic distribution. The characteristic distribution may be generated as image data that indicates the characteristic information inside the subject. The image data may be generated as three-dimensional volume data by reconstructing an image, for example.

By enhancing the portion which indicates the absorption coefficients characteristic to the blood, the blood vessel structure inside the subject can be visualized as an image. In this case, the distribution of arteries and the distribution of veins can be visualized as an image respectively based on the oxygen saturation degree.

The "acoustic wave" in the present invention is typically an ultrasonic wave, including an elastic wave called a "sound wave" or a "photoacoustic wave". A signal (e.g. electric signal) converted from an acoustic wave by a transducer or the like is called an "acoustic signal" or a "received signal". Such terms as "ultrasonic wave" or "acoustic wave" herein, however, are not intended to limit the wavelength of the elastic wave. An acoustic wave generated by the photoacoustic effect is called a "photoacoustic wave" or a "light-induced ultrasonic wave". A signal (e.g. electric signal) derived from a photoacoustic wave is called a "photoacoustic signal". An image generated from the photoacoustic signal by image reconstruction or the like is called a "photoacoustic image".

It is under consideration that when the skin flap sampling surgery is performed, a photoacoustic image (vascular image) is acquired by performing the photoacoustic measurement on the skin flap sampling area, and the positions and running state of the blood vessels are recognized from this vascular image, so as to facilitate determination of the position and range of the flap to be sampled. In this case, the operator must recognize which part of the subject corresponds to the vascular image. However, a region of which surface has no major features in a relatively wide range, such as a femoral region, is normally used for the skin flap sampling. Therefore it tends to be difficult to specify the positional relationship between the vascular image and the actual subject.

Therefore in the following embodiments, the correspondence between the position in the subject and the photoacoustic image is clearly presented to the operator, so as that the correspondence between the photoacoustic image and the subject can be easily recognized. Thereby the operator can recognize the actual position of the blood vessel (e.g. perforator) in the subject based on the vascular image, and can sample the skin flap easily.

Embodiment 1

The basic concept of the embodiment will be described here. In Embodiment 1, markers are directly disposed on the subject. FIG. 1 is a conceptual diagram of a subject information acquisition apparatus 1 according to Embodiment 1.

(Configuration of Apparatus)

A subject 2 is held by a holding member 200. An acoustic matching medium (not illustrated) may be filled in a space between the subject 2 and the holding member 200, so that the acoustic wave can be transferred easily. The acoustic matching medium is, for example, water, gel or the like. The preferred material of the holding member is a material of which acoustic impedance is close to the human body, and the transmittance is high with respect to the light and acoustic waves. For example, polymethyl-pentene, polyethylene terephthalate and acrylic are preferred. A mesh member may be used for the holding member in order to prevent a drop in the S/N ratio caused by multiple reflections of the acoustic wave. For the material of the mesh member, metal, fiber, resin or the like can be used.

The holding member 200 combining the mesh member with a film member or a sheet member may be used. In this case, the film or sheet member formed of resin, for example, is disposed on the upper side (subject side) or the lower side (conversion elements side) of the mesh member. Thereby the subject can be held even if the film member is thin, which improves the transmissivity of the light and acoustic wave. Further, the film member can separate the acoustic matching member filling the space between the subject side and the conversion element side, hence clearness improves and the acoustic matching medium can be more easily exchanged. The frame member to support the film is not limited to mesh, but may be an umbrella rib form.

The light emitted from a light source 100 is radiated from the emission end 140 below the support body via an optical transmission line 120. The optical transmission line 120 is constituted of such optical members as an optical fiber, mirror, prism and lens. When the irradiation light is absorbed by a light absorber inside the object, on the surface of the object, or on the holding member 200, a photoacoustic wave is generated. A plurality of conversion elements 320 supported by the support body 300 receives the photoacoustic wave, and converts the photoacoustic wave into electric signals (photoacoustic signals).

The light source 100 emits light of which pulse duration is about 1 to 100 nanoseconds in order to efficiently generate the photoacoustic wave. If the subject is a living body, the wavelength of the light is preferably 600 nm to 1,100 nm. For the light source 100, an Nd:YAG laser, an alexandrite laser, a Ti-sa laser and an OPO laser, for example, can be used. An LED and semiconductor laser can also be used. By using the light source 100 that can emit a plurality of wavelengths of light, such as a wavelength-variable laser, the concentration of the substance inside the object (e.g. oxygen saturation degree) can be acquired.

The support body 300 is a hemispherical member formed of metal, resin or the like. The plurality of conversion elements 320 are disposed on the support body 300 such that a high sensitivity region, where directional axes converge, is formed. The structures of the holding member and the support body are not limited to the above. For example, a plate type holding member that holds the subject by pressing may be used. The conversion element may be a single element, or may be arrayed linearly or two-dimensionally. The acoustic matching medium (not illustrated) that allows the acoustic wave to propagate is disposed between the holding member and the conversion elements. The acoustic matching medium is water or gel, for example.

A camera 500 is an optical imaging apparatus that is disposed on the conversion element side with respect to the subject. The camera 500 optically captures an image of a target region of the photoacoustic measurement using visible light, infrared light or the like, and sends the acquired optical image to the information processing apparatus as image data.

A driving unit 600 controls a moving mechanism (not illustrated) constituted of a driving stage and other components, to move the support body relative to the subject. By performing the photoacoustic measurement at a plurality of positions to which the driving unit 600 moved the support body, a photoacoustic image in a wide region of the subject can be acquired. The driving unit 600 moves the support body 300 on the moving plate below the subject using such a method as spiral scan and raster scan. Then light irradiation and reception of the photoacoustic wave are repeated at a predetermined cycle. The driving unit sends the irradiation positions with the pulsed light to the reconstruction unit.

A signal acquisition unit 400 amplifies photoacoustic signals, which are sequentially outputted from the conversion elements that received the photoacoustic wave, converts the amplified photoacoustic signals into digital signals, and sends the digital signals to the reconstruction unit 840. The signal acquisition unit 400 is constituted of an amplifier, an AD convertor and other components.

The information processing apparatus 800 includes such functional blocks as a control unit 810, an optical image acquisition unit 820, a reconstruction unit 840, an image processing unit 850 and a storage unit 870. For the information processing apparatus 800, a computer or workstation, which includes such arithmetic resources as a processor and memory and operates according to the instructions of the program, can be used. The information processing apparatus 800 need not always include a specific components (e.g. processing circuit) corresponding to each functional block. Each functional block may be virtually implemented as a program module which performs respective processing. It is not always necessary to include all the functional blocks in one computer, but a plurality of computers, which are connected communicably, may constitute the information processing apparatus 800 collaboratively.

The control unit 810 controls the operation of each component of the subject information acquisition apparatus 1, light irradiation timing of the light source 100, signal acquisition timing by the conversion elements 320, position and speed of the driving unit 600 to move the support body 300, timing of the optical imaging and imaging method thereof performed by the camera 500, among other operations. The optical image acquisition unit 820 receive image data from the camera 500, performs processing (e.g. correction) if necessary, and stores the image data in the storage unit.

The reconstruction unit 840 reconstructs the image based on the photoacoustic signal from the signal acquisition unit 400 and the photoacoustic signal acquisition position information from the driving unit 600, and acquires the characteristic information distribution on the target region of the subject. For the image reconstruction, such a method as a phase addition method and a Fourier transform method can be used. The acquired characteristic information distribution is sent to the image processing unit 850. The reconstruction unit 840 is equivalent to the photoacoustic image acquisition unit of the present invention. The image processing unit 850 generates a display image by the later mentioned superimposing processing.

The storage unit 870 temporarily or permanently stores data generated along with the operation of the subject information acquisition apparatus 1, such as control information by the control unit 810, photoacoustic signals, image data of optical images, reconstructed characteristic information distribution data, and the later mentioned image data processed by the image processing unit 850, and outputs the data when necessary.

The input unit 880 is a unit for the user (e.g. operator) to input instruction information, and the user interface (e.g. mouse, keyboard, touch panel) of the information processing apparatus 800, for example, can be used for the input unit 880. For the display unit 900, such a display apparatus as a liquid crystal display and organic EL display can be used.

(Process flow)

Figure 2:
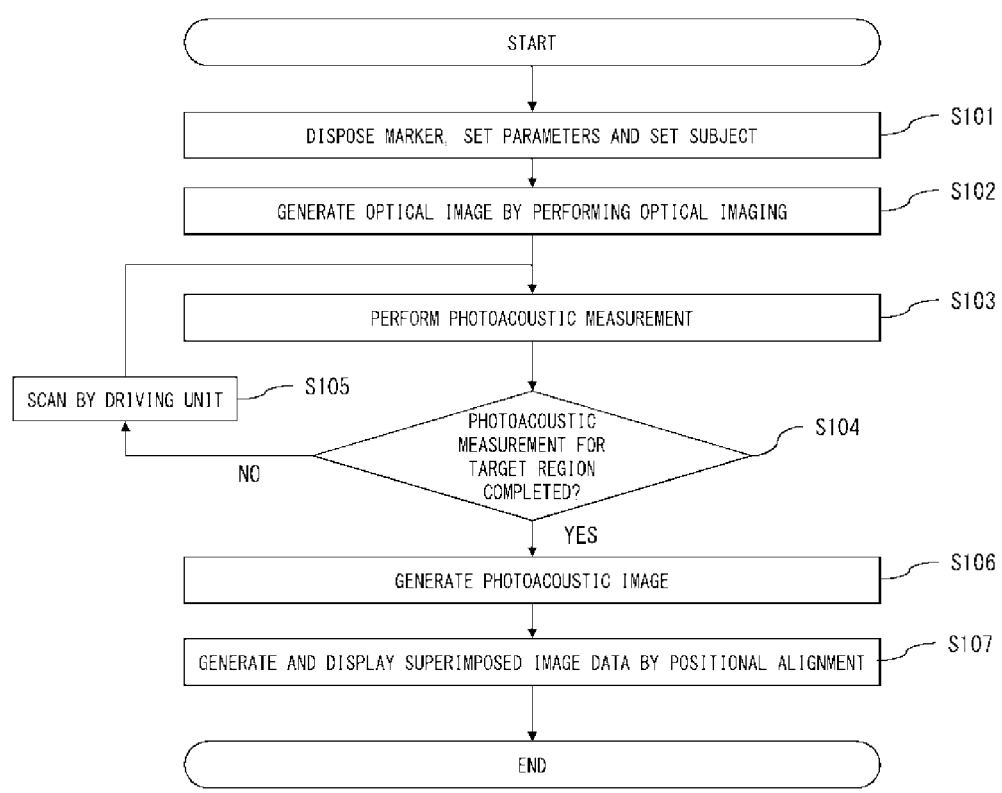
FIG. 2 is a flow chart of the processing according to Embodiment 1.

The general flow of processing according to Embodiment 1 will be described with reference to FIG. 2. In step S101, the user disposes markers 250 at predetermined locations. The marker 250 is a light absorber that absorbs light and generates an acoustic wave. The arrangement, positions, types and materials of the markers will be described later. Then the user sets the parameters related to the operation of the apparatus. The parameters include specifications on the creation of superimposed images, such as the imaging target region on the subject, the route and speed of scanning by the driving unit 600, the intensity and intervals of light irradiation when the photoacoustic measurement is performed, and the image quality of the photoacoustic image and optical image. Then the user sets the subject in the holding member 200.

In step S102, the camera 500 performs the optical imaging in accordance with the parameters. Then the optical image acquisition unit 820 acquires an optical image. In step S103, the photoacoustic measurement is performed. In concrete terms, the light source 100 emits light, and the conversion elements 320 receives the photoacoustic wave, and outputs the photoacoustic signals. The photoacoustic signals are stored in the storage unit 870.

In step S104, the control unit 810 determines whether the photoacoustic measurement for the target region completed. Processing advances to step S106 if completed (YES). If not (NO), processing advances to step S105 where the support body 300 is scanned by the driving unit 600, and the photoacoustic measurement is performed at the next position. In step S106, the reconstruction unit 840 generates the photoacoustic image of the target region and stores the photoacoustic image in the storage unit 870. In step S107, the image processing unit 850 generates the superimposed image data, and displays the superimposed image data on the display unit 900.

(Superimposing of Images)

The method of superimposing and displaying the photoacoustic image and the optical image will be described in the sequence of steps (1) to (4). In Embodiment 1, the markers 250 (light absorbers) are disposed directly on the subject.

(Step 1) Disposing Markers

Figure 3:
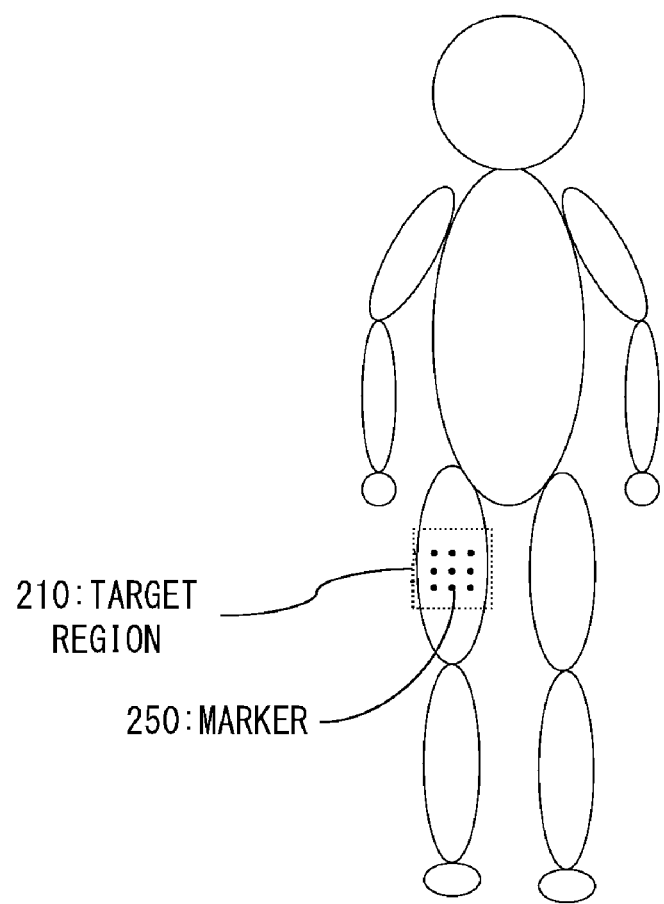
FIG. 3 is a diagram depicting a state of disposing markers in a target region of the subject.

This step corresponds to step S101. The user disposes a plurality of markers on the target region 210, which is an imaging area of photoacoustic measurement and optical imaging, and is a target of the superimposed image generation, as illustrated in FIG. 3.

For the marker 250, a material that has an absorption characteristic at a wavelength used for the photoacoustic measurement is used. For example, black ink can be used. In this case, the user directly writes the markers on the subject using a pen containing black ink. The marker 250, however, is not limited to this, but may be any material that can be disposed on both the photoacoustic image and optical image. For example, a seal that contains a light absorber (e.g. carbon) can be used. The light absorber (e.g. carbon) may be attached to the subject using an adhesive. The intensity of the photoacoustic wave generated from the marker is preferably an intensity similar to the intensity of the photoacoustic wave generated from the imaging area, or smaller than the intensity by one digit. Considering that the absorption coefficient of hemoglobin, which is a typical substance that absorbs light inside the object, is 0.3/mm to 0.9/mm, it is preferable that the absorption coefficient of the marker is an absorption coefficient that is at least 0.05/mm and not more than 1.0/mm.

The shape of the marker 250 is not limited to a dot, but may be a line, a matrix, a radial or a circular shape, and may be selected in accordance with the intended use and size of the target region.

Instead of the markers disposed by the user or in addition to the markers disposed by the user, a portion of the subject where the light absorption is high may be used as a marker. For example, an area where pigments concentrate (e.g. a mole) is such a portion.

(Step 2) Acquiring Optical Image

Figure 4:
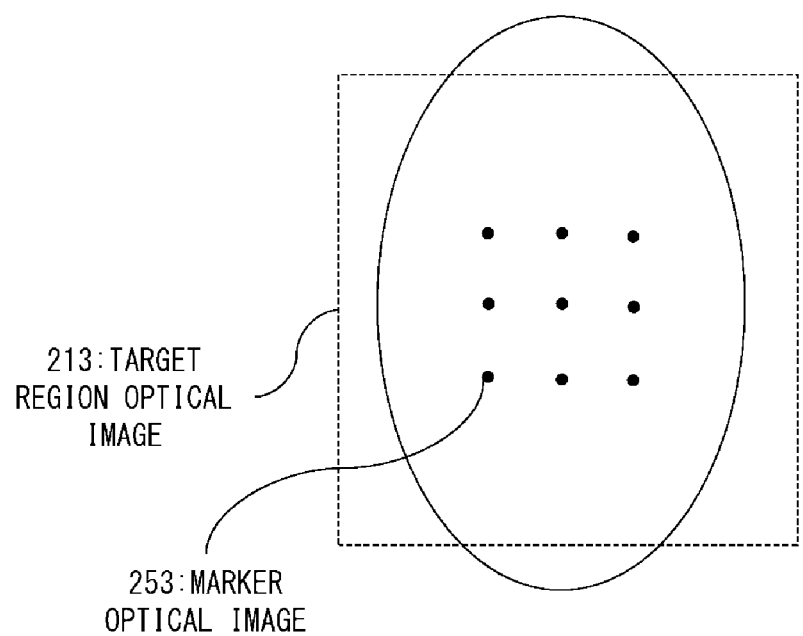
FIG. 4 is a diagram depicting an example of an optical image.

This step corresponds to step S102. The camera 500 adjusts such that all the markers 250 disposed in the target region 210 are included in the imaging visual field, and performs optical imaging. The optical image acquisition unit 820 receives image data, and stores the image data to the storage unit 870 after performing correction processing if necessary. FIG. 4 is a schematic diagram of an optical image (target region optical image 213). It is desirable that the markers (marker optical image 253) are captured clearly so that positional alignment is possible. Furthermore, it is necessary for the structural characteristics, such as contour lines, are imaged so that the user can recognize which area of the subject corresponds to the target region. In the case of an image of a femoral region, as illustrated in FIG. 4, if the contour lines at the left and right are imaged, the target region can be easily recognize based on the direction and thickness of the contour lines.

(Step 3) Acquiring Photoacoustic Image

Figure 5:
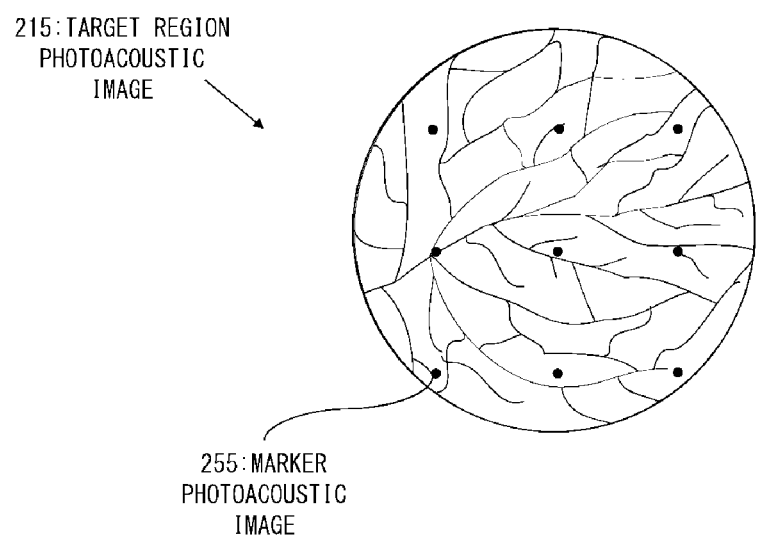
FIG. 5 is a diagram depicting an example of a photoacoustic image.

This step corresponds to steps S103 and S106. As mentioned above, the photoacoustic wave generated by light irradiation from the light source 100 includes components derived from the markers 250 along with the components derived from the subject. Therefore the photoacoustic image generated by the reconstruction unit 840 (target region photoacoustic image 215 in FIG. 5) also includes an image derived from the markers (marker photoacoustic image 255 in FIG. 5), in addition to the image derived from the blood vessels in the target region.

(Step 4) Superimposing Processing

Figure 6:
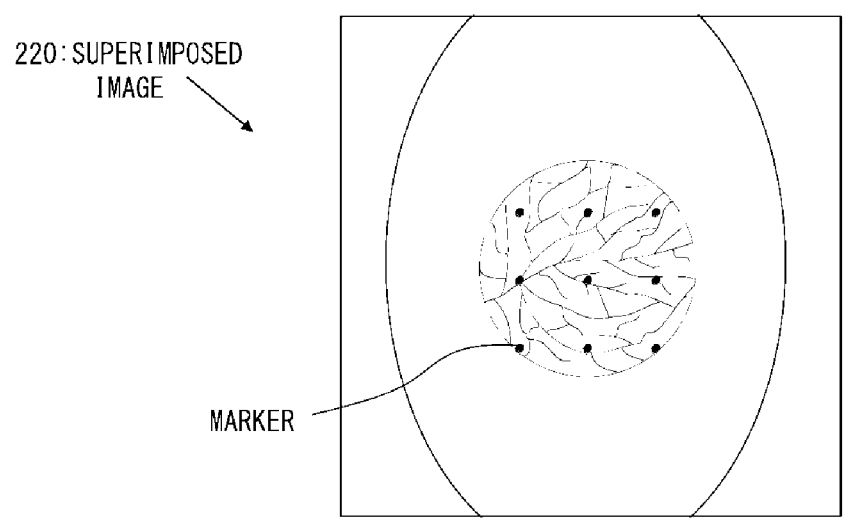
FIG. 6 is a diagram depicting an example of a superimposed image.

This step corresponds to step S107. After matching the sizes of the photoacoustic image and the optical image, the image processing unit 850 aligns the positions based on the marker optical image 253 and the marker photoacoustic image 255, so as to generate the superimposed image 220, as illustrated in FIG. 6. When the photoacoustic image and the optical image are superimposed, if the direction or position of the subject of the photoacoustic image and that of the optical image are different, at least one of these images may be rotated or moved. For this processing, various known methods may be used.

According to Embodiment 1, the photoacoustic image and the optical image can be accurately superimposed based on the positions of the markers. As a result, the user can accurately recognize the correspondence between the vascular image captured in the photoacoustic image and the portion of the subject based on such information as the contour lines of the subject.

Embodiment 2

In Embodiment 2, the markers 250 are disposed not only on the subject, but on the holding member. In the following, differences from Embodiment 1 will be primarily described.

Figure 7:
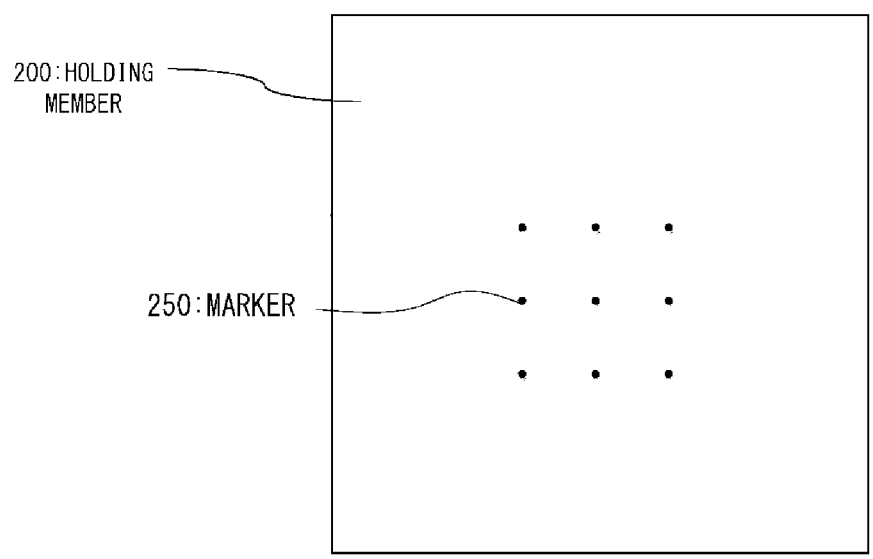
FIG. 7 is a diagram depicting a state where the markers are disposed on a holding member according to Embodiment 2.

FIG. 7 indicates the holding member 200 of Embodiment 2. As illustrated, the markers 250 are disposed on the holding member 200. For the holding member 200 and the markers 250, the same materials as Embodiment 1 can be used. To dispose the markers 250 on the holding member 200 as well, such a method as writing with a pen, attaching seals as the markers 250, or adhering the markers with adhesive can be used, just like Embodiment 1. Further, in the case of Embodiment 2, the markers 250 may be embedded in advance when the holding member 200 is manufactured. The markers may be formed of any material as long as the markers can be confirmed in both the optical image and the photoacoustic image. For example, carbon black may be used.

Photoacoustic measurement, optical imaging and superimposed image generation are the same as Embodiment 1. In other words, the camera 500 images the subject along with the holding member 200 on which the markers 250 are disposed. The photoelectric wave that the conversion elements 320 receive includes components derived from the subject and components derived from the markers 250 on the holding member. The image processing unit 850 superimposes the photoacoustic image and the optical image using the markers as alignment marks, so as to generate the superimposed image 220.

In Embodiment 2, the markers 250 are not disposed on the subject. Therefore it is preferable that positioning markers, to position the imaging area of the subject, are separately disposed on the subject side. For the positioning markers, alignment marks written or adhered to the imaging area of the subject may be used, or such a physical characteristic as a mole may be used. The positioning markers need not generate the photoacoustic wave. Using the positioning markers, the user makes an adjustment before optical imaging, so that the imaging area comes to a desired position in the visual field of the camera.

By Embodiment 2 as well, the correspondence between the blood vessels captured in the photoacoustic image and an area of the subject can be accurately recognized based on the contours or the like of the subject.

Embodiment 3

The markers 250 are written in the superimposed image 220 acquired in the above mentioned Embodiments 1 and 2. These markers have an advantage in that the positions are more easily recognized, but there is also a problem in that visibility of the user drops. Therefore in Embodiment 3, a method of deleting the markers from the display image will be described. In each modification below, a method of the reconstruction unit 840 deleting or reducing the components derived from the markers in the photoacoustic image will be described.

The image processing unit 850, on the other hand, removes the markers from the optical image, or at least reduces the components derived from the markers. In concrete terms, the image processing unit 850 determines the range of the markers in the optical image by performing image processing based on the pixel values, or on the range that the user specified via the input unit 880. Then the pixel values in the determined range of the markers are corrected based on the interpolation of the values of the peripheral pixels. Normally, it is sufficient if a general structure, such as the contour lines, can be recognized in an optical image, and little of the detailed structure on the surface of the subject need be displayed. Hence the resolution of the surface of the subject that includes the markers may be decreased, or the entire femoral region may be filled with a uniform color.

The image processing unit 850 superimposes the photoacoustic image and the optical image after deleting the markers. In this case as well, superimposing processing can be executed without problems, since the positions of the markers in the images have already been recognized. The image processing unit 850 may superimpose the photoacoustic image and the optical image without deleting the markers, then delete the markers from the superimposed image.

(Modification 1) Deleting Information on Surface

In some cases, when the user wants to see the vascular image inside the subject, information on the surface of the subject may be unnecessary. Therefore in Modification 1, data corresponding to the surface of the subject is deleted from the photoacoustic signals and the photoacoustic image. For example, a case where volume data from the surface of the target region of the subject to a 5 cm depth was acquired by image reconstruction will be described. In this case, the markers in the display image can be deleted by excluding the volume data at 2 mm from the surface of the object. The volume data in this depth range may be deleted, or an identifier to not display the data on the screen may be attached to this data at this depth range, for example. In the case of disposing the markers on the holding member, as in Embodiment 2, the data for the thickness of the holding member may be removed from the display target. Any method may be used to generate a two-dimensional image for display from the volume data. For example, the image data having a predetermined depth may be extracted based on the surface of the object. An MIP image may be generated. A tomographic image having a predetermined depth may be selected. In this case, it is not necessary to generate all the volume data.

Further, instead of deleting the data of the surface portion after the volume data is generated, components derived from the markers may be deleted from the photoacoustic signals in advance. A portion of a photoacoustic signals stored in the storage unit derived from the markers can be calculated based on the light irradiation timing, the acoustic matching medium and the sound velocity of the subject. By reconstructing an image using such photoacoustic signals, a photoacoustic image without markers can be generated.

(Modification 2) Subtracting Marker Information

In Modification 2, the marker shape is stored in the storage unit in advance, and the markers having this shape are deleted by performing image processing when the image is displayed. In the case of disposing the markers on the holding member, as in Embodiment 2, only the markers are photoacoustic-measured in advance in the state where the subject is not set on the holding member, and the components of the photoacoustic signals derived from the markers are stored in the storage unit, then the stored components are removed from the photoacoustic image.

(Modification 3) Using Difference of Oxygen Saturation Degree

In Modification 3, the vascular image and the markers are identified based on the oxygen saturation degree values in the photoacoustic image, and the image is displayed without the markers. The light source in Modification 3 can emit light with a plurality of wavelengths, including a first wavelength and a second wavelength. Based on the absorption coefficient distribution of each wavelength, the reconstruction unit generates image data representing the oxygen saturation degree distribution, utilizing the difference of the absorption coefficients of oxyhemoglobin and deoxyhemoglobin for each wavelength. For example, the oxygen saturation degree of the arterial blood is normally about 95%, and the oxygen saturation degree of the venous blood is about 75%. Therefore if a material of which oxygen saturation degree calculated at a wavelength of the irradiation light is even lower than that of venous blood (e.g. material of which oxygen saturation degree is 20% or less), the vascular image and the markers are distinguishable from each other.

Modification 4) Using Difference of Absorption Spectra

It is also possible to perform image processing using markers having an absorption spectrum that is different from that of hemoglobin when the wavelength variable light source is used. For example, a light source that can emit light having a wavelength (first wavelength), which is easily absorbed by hemoglobin, and light having a wavelength (second wavelength), which is not easily absorbed by hemoglobin but is easily absorbed by the markers, is used. In other words, for at least two wavelengths, a wavelength and the material of the markers, by which the greater or lesser relationship of the absorption coefficients of the hemoglobin and the markers reverses, are selected. For positioning with the optical image using the markers, the photoacoustic image derived from the second wavelength is used, then the accuracy of the positioning improves. The photoacoustic image derived from the second wavelength can also be used to remove the marker information from the photoacoustic image derived from the first wavelength. By Modification 4 as well, the vascular image and the markers can be identified, whereby the markers can be removed from the display image.

In the case of using a light source having a plurality of wavelengths, as in Modifications 3 and 4, displacement due to body motion can be reduced by emitting light having a plurality of wavelengths alternately in a single measurement, rather than completing measurement initially with a first wavelength, then executing measurement with the next wavelength.

Figure 8:
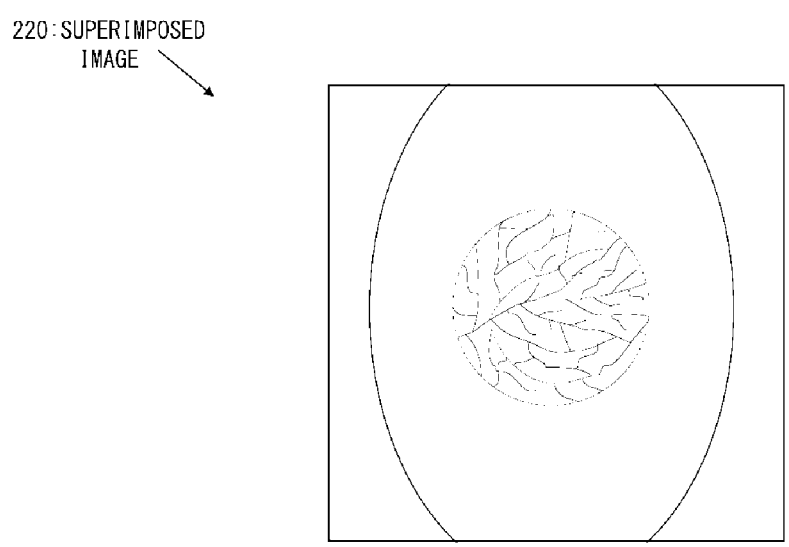
FIG. 8 is a diagram depicting an example of a superimposed image according to Embodiment 3.

According to Embodiment 3, the superimposed image, in which the vascular image can more easily be observed without marker information, can be displayed, as illustrated in FIG. 8, and thereby visibility of the user improves. On the other hand, the contour lines of the subject remain, hence the positional relationship between the vascular image and the subject can still be recognized without problems.

Embodiment 4

Figure 9:
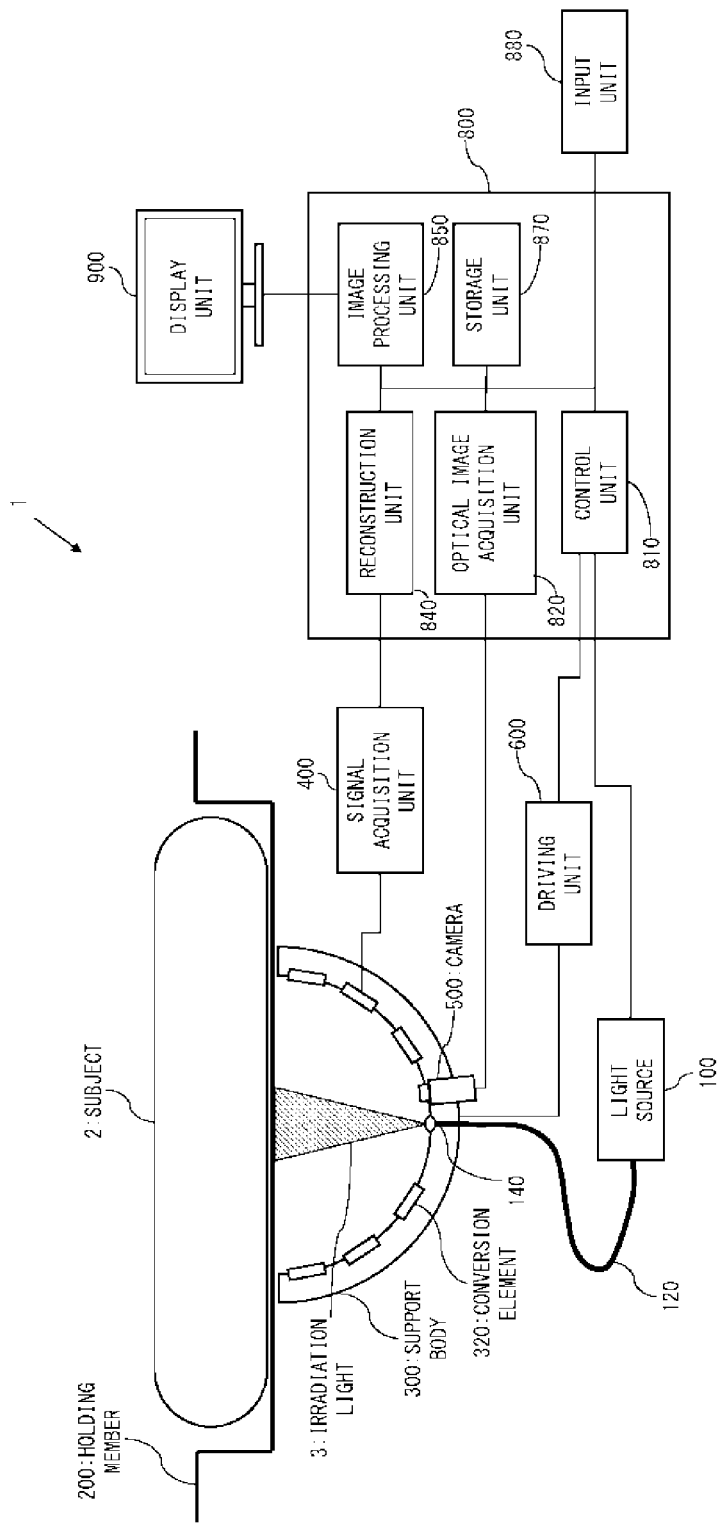
FIG. 9 is a conceptual diagram of a subject information acquisition apparatus according to Embodiment 4.

In Embodiment 4, a modification of a method of acquiring the optical image will be described. In the case of the apparatus configuration in FIG. 1, the support body 300 is disposed between the camera 500 and the subject during the photoacoustic measurement, hence optical imaging cannot be performed. Therefore in Embodiment 4, the apparatus configuration is modified as illustrated in FIG. 9, so that the optical imaging can be performed even during the photoacoustic measurement. In FIG. 9, the camera 500 is disposed with the conversion elements 320 on the support body 300, and images are captured while being moved by the driving unit 600.

In Embodiment 4, the visual field of the camera 500 during optical imaging is smaller compared with the configuration of Embodiment 1, hence the target region of the subject cannot be imaged all at once. Therefore the optical image acquisition unit 820 of Embodiment 4 combines a plurality of optical images, so as to create an optical image of the entire target region. In concrete terms, the camera 500 performs optical imaging a plurality of times while moving, and stores the acquired optical images in the storage unit 870 sequentially. The optical image acquisition unit 820 performs combining processing based on the position information of the support body 300, which is received from the driving unit 600 via the control unit 810 and each timing when the camera 500 acquired the plurality of optical images respectively, so as to generate one optical image.

Figure 10A:
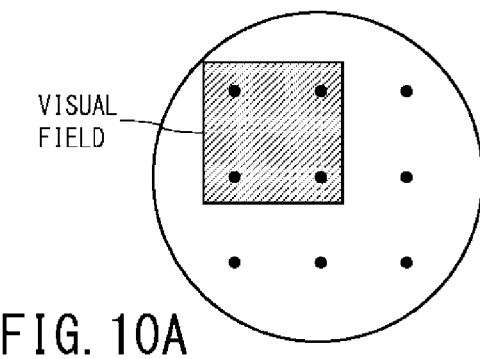
FIGS. 10A to 10E represent conceptual diagrams depicting composite image generation according to Embodiment 4.
Figure 10B:
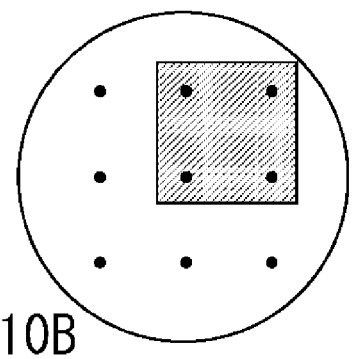
Figure 10C:
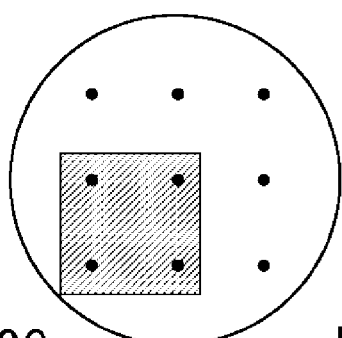
Figure 10D:
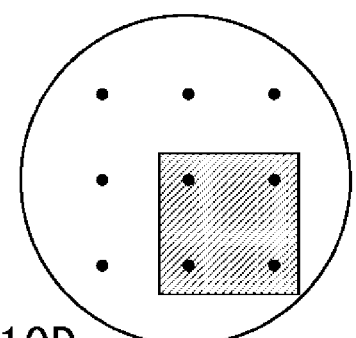
Figure 10E:
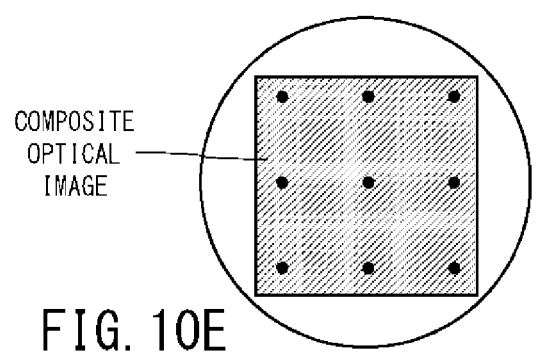

As illustrated in FIGS. 10A to 10D, the composite optical image illustrated in FIG. 10E can be easily generated if a plurality of (two or more) markers are arranged at intervals which allow the markers to be included in the visual field of the camera. Such an arrangement method can be applied when the markers are disposed on the holding member side or on the subject side.

Figure 11A:
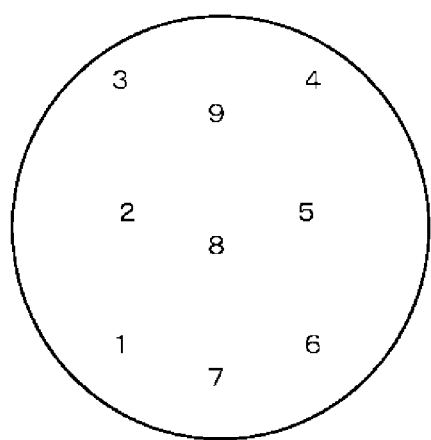
FIGS. 11A and 11B represent diagrams depicting different examples of the markers according to Embodiment 4.
Figure 11B:
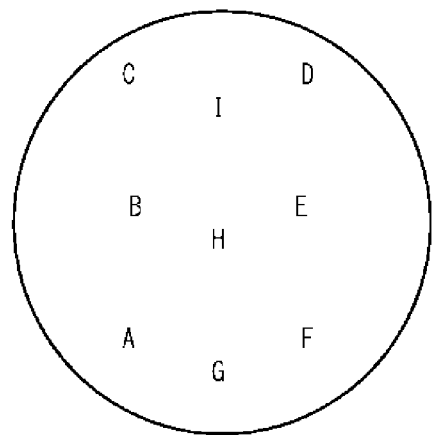

In FIGS. 11A and 11B, examples of the markers of Embodiment 4 are illustrated. If the examples of FIGS. 11A and 11B are used, the position of each marker is uniquely identified, which makes it easy to generate the composite optical image. The shapes and types of the markers are not limited to those in FIGS. 10A to 10D and FIGS. 11A and 11B.

Embodiment 5

In Embodiment 5, a preferable example of generating the superimposed image using the image processing unit 850 will be described. When one of the optical image and the photoacoustic image is superimposed on the other, the image processing unit 850 of Embodiment 5 changes the transparency of at least one of the images.

In the following example, it is assumed that the subject is a femoral region, the photoacoustic image to be generated is a vascular image, and the photoacoustic image is superimposed on the optical image. The image processing unit 850 converts the sizes of both images so as to match, then changes the transparency of the photoacoustic image to 50%, and superimposes the photoacoustic image on the optical image. Thereby the image of the blood vessels flowing in the femoral region (subject) can be clearly recognized. Which image is on top of the other, and the transparency of each image can be arbitrarily set depending on the intended use.

Embodiment 6

The present invention may be regarded as a display method that is executed by the information processing apparatus 800 to superimpose and display a photoacoustic image and an optical image. In this case, the information processing apparatus 800 acquires photoacoustic signals that include components derived from the markers and components derived from the subject (or photoacoustic image generated from the photoacoustic signals), and acquires an optical image of the same subject captured by camera. Then, these images are superimposed using the markers as reference, and the generated superimposed image is displayed.

As described above, the present invention can assist the user to understand the correspondence between the photoacoustic image and the subject. As a result, even if the subject has a large surface area or has no major features in the structure, the operator can easily recognize the vascular structure of the subject.

According to the present invention, a technique to easily recognize the correspondence between a photoacoustic image and a subject can be provided.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™, a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An image information processing apparatus comprising:
    a memory storing a program; and
    one or more processors which, by executing the program, function as:
    a photoacoustic image acquisition unit configured to acquire a photoacoustic image generated based on a photoacoustic wave by irradiating a subject and a marker with light;
    an optical image acquisition unit configured to acquire an optical image generated by optically capturing an image of the subject and the marker; and
    an image processing unit configured to generate a superimposed image, based on the marker in the photoacoustic image and the marker in the optical image, in which the photoacoustic image and the optical image are superimposed and display the superimposed image on a display unit,
    the image processing unit generating an image from the superimposed image and displaying the generated image on the display unit, wherein a component, of the generated image, derived from the marker is reduced,
    wherein the light includes a plurality of wavelengths of light, and
    wherein the image processing unit reduces the component, of the generated image, derived from the marker based on a difference between a property of the marker acquired by irradiation of the plurality of wavelengths of light and a property of the subject acquired by the irradiation of the plurality of wavelengths of light.

2. The image information processing apparatus according to claim 1, further comprising:
    a support body configured to support a conversion element for receiving the photoacoustic wave and a camera for capturing the optical image; and
    a driving unit configured to move the support body relative to the subject.

3. The image information processing apparatus according to claim 2, wherein the optical image acquisition unit acquires the optical image by superimposing a plurality of images captured at a plurality of positions to which the driving unit moves the camera.

4. The image information processing apparatus according to claim 3, wherein the marker is disposed at two or more positions included in a visual field of the camera.

5. The image information processing apparatus according to claim 1, wherein the marker is a material having an absorption characteristic at a wavelength of the light.

6. The image information processing apparatus according to claim 1, wherein the marker is a marker on the subject.

7. The image information processing apparatus according to claim 6, wherein the marker is disposed at a portion of the subject where a pigment concentrates.

8. The image information processing apparatus according to claim 1, further comprising:
    a holding member configured to hold the subject,
    wherein the marker is disposed on the holding member.

9. The image information processing apparatus according to claim 1, wherein the image processing unit generates the superimposed image by matching a size of the photoacoustic image and a size of the optical image.

10. The image information processing apparatus according to claim 1, wherein the image processing unit reduces from the photoacoustic image a component derived from a surface of the subject including the marker.

11. The image information processing apparatus according to claim 1, wherein the image processing unit reduces from the photoacoustic image a component derived from the marker by performing image processing based on a shape of the marker.

12. The image information processing apparatus according to claim 1, wherein the property is an oxygen saturation degree.

13. The image information processing apparatus according to claim 1, wherein the property is an absorption spectrum.

14. A display method comprising:
    a photoacoustic image acquisition step of acquiring a photoacoustic image generated based on a photoacoustic wave by irradiating a subject and a marker with light;
    an optical image acquisition step of acquiring an optical image generated by optically capturing an image of the subject and the marker; and
    an image processing step of generating a superimposed image, based on the marker in the photoacoustic image and the marker in the optical image, in which the photoacoustic image and the optical image are superimposed and display the superimposed image on a display unit,
    the image processing step generating an image from the superimposed image and displaying the generated image on the display unit, wherein a component, of the generated image, derived from the marker is reduced,
    wherein the light includes a plurality of wavelengths of light, and
    wherein the image processing step reduces the component, of the generated image, derived from the marker based on a difference between a property of the marker acquired by irradiation of the plurality of wavelengths of light and a property of the subject acquired by the irradiation of the plurality of wavelengths of light.

15. The display method according to claim 14, further comprising:
    a driving step of moving a support body relative to the subject, the support body being configured to support a conversion element for receiving the photoacoustic wave and a camera for capturing the optical image, and
    the optical image acquisition step acquires the optical image by superimposing a plurality of images captured at a plurality of positions to which the driving step moves the camera.

16. The display method according to claim 14, wherein the image processing step generates the superimposed image by matching a size of the photoacoustic image and a size of the optical image.

17. The display method according to claim 14, wherein the image processing step reduces from the photoacoustic image a component derived from a surface of the subject including the marker.

18. The display method according to claim 17, wherein the image processing step reduces from the photoacoustic image a component derived from the marker by performing image processing based on a shape of the marker.

19. The display method according to claim 14, wherein the property is an oxygen saturation degree.

20. The display method according to claim 14, wherein the property is an absorption spectrum.

21. A non-transitory computer-readable medium storing a program for causing a computer to execute the display method according to claim 14.

22. An image information processing apparatus comprising:
a memory storing a program; and
one or more processors which, by executing the program, function as:
a photoacoustic image acquisition unit configured to acquire a photoacoustic image generated based on a photoacoustic wave by irradiating a subject and a marker with light;
an optical image acquisition unit configured to acquire an optical image generated by optically capturing an image of the subject and the marker; and
an image processing unit configured to generate a superimposed image, based on the marker in the photoacoustic image and the marker in the optical image, in which the photoacoustic image and the optical image are superimposed and display the superimposed image on a display unit,
the image processing unit generating an image from the superimposed image and displaying the generated image on the display unit, wherein a component, of the generated image, derived from a surface of the subject including the marker is reduced,
wherein the light includes a plurality of wavelengths of light, and
wherein the image processing unit reduces the component, of the generated image, derived from the surface of the subject including the marker based on a difference between a property of the marker acquired by irradiation of the plurality of wavelengths of light and a property of the subject acquired by the irradiation of the plurality of wavelengths of light.

23. A display method comprising:
a photoacoustic image acquisition step of acquiring a photoacoustic image generated based on a photoacoustic wave by irradiating a subject and a marker with light;
an optical image acquisition step of acquiring an optical image generated by optically capturing an image of the subject and the marker; and
an image processing step of generating a superimposed image, based on the marker in the photoacoustic image and the marker in the optical image, in which the photoacoustic image and the optical image are superimposed and display the superimposed image on a display unit,
the image processing step generating an image from the superimposed image and displaying the generated image on the display unit, wherein a component, of the generated image, derived from a surface of the subject including the marker is reduced,
wherein the light includes a plurality of wavelengths of light, and
wherein the image processing step reduces the component, of the generated image, derived from the surface of the subject including the marker based on a difference between a property of the marker acquired by irradiation of the plurality of wavelengths of light and a property of the subject acquired by the irradiation of the plurality of wavelengths of light.

* * * * *